US00PP11715P

United States Patent [19]

Zary

[11] Patent Number: Plant 11,715

[45] Date of Patent: Dec. 26, 2000

[54] HYBRID TEA ROSE PLANT NAMED 'JACROVE'

[75] Inventor: Keith W. Zary, Thousand Oaks, Calif.

[73] Assignee: Bear Creek Gardens, Inc., Medford, Oreg.

[21] Appl. No.: 09/215,792

[22] Filed: Dec. 18, 1998

[51] Int. Cl.[7] ..... A01H 5/00

[52] U.S. Cl. ..... Plt./139

[58] Field of Search ..... Plt./136, 139, 138, Plt./148, 150

[56] References Cited

U.S. PATENT DOCUMENTS

| | | | |
|---|---|---|---|
| P.P. 2,959 | 1/1970 | Brownell | Plt./139 |
| P.P. 8,633 | 3/1994 | Zary | Plt./139 |
| P.P. 11,020 | 8/1999 | Evers | Plt./139 |

*Primary Examiner*—Howard J. Locker
*Attorney, Agent, or Firm*—Klarquist Sparkman Campbell Leigh & Whinston, LLP

[57] ABSTRACT

Hybrid tea rose plant having the large, bright red flowers; upright, well-branched growth habit; dark green, glossy foliage; and disease resistance to rose rust, but susceptibility to powdery mildew and blackspot.

1 Drawing Sheet

The present invention relates to a new and distinct variety of rose plant of the hybrid tea class which was originated by me by crossing the variety 'JACreb' (not patented), with 'JACtwin' (U.S. Plant Pat. No. 4,437).

The primary objective of this breeding was to produce a new rose variety having the large, bright red flowers of the female parent combined with the more compact growth and vigorous, upright habit of the male parent. The objective was substantially achieved, along with other desirable improvements, as evidenced by the following unique combination of characteristics that are outstanding in the new variety and that distinguish it from its parents, as well as from all other varieties of which I am aware:

1. Large, bright red flowers;
2. Upright, well-branched growth habit;
3. Dark green, glossy foliage; and
4. Resistance to rose rust, but susceptibility to powdery mildew.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACred' (not patented) (unnamed red seedling×'HILroy').

*Pollen parent.*—*'JACtwin', U.S. Plant Pat. No.* 4,437.

Classification:

*Botanical.*—*Rose hybrida.*

*Commercial.*—Hybrid Tea.

FLOWER

Observations made from specimens grown in a garden environment at Somis, Calif. from January 1997 to October 1998.

Blooming habit: Continuous.

Bud:

*Size.*—1¾–2 inches long when the petals start to unfurl.

*Form.*—The bud form is long, pointed ovoid.

*Color.*—When sepals first divide, the bud color is Red Group 42A. When half blown, the upper and lower sides of the petals are Red Group 42A.

*Sepals.*—Color: Green Group 138B blushed with Greyed-Purple 183D when exposed to bright sun. Surface texture: Covered in fine hairs. There are three lightly appendaged sepals. There are two unappendaged sepals with hairy edges.

*Receptacle.*—Color: Green Group 137A and Greyed-Purple 183A when exposed to bright sun. Shape: Funnel. Size: Medium (7/16" long×5/16" wide). Surface: Smooth.

*Peduncle.*—Length: Short (averaging 2½"). Surface: Smooth. Color: Greyed-Purple Group 183A when exposed to bright sun; otherwise Green Group 137C. Strength: Stiff, erect.

Bloom:

*Size.*—Large. Average open size is 4½ inches.

*Borne.*—Singly.

*Stems.*—Strength: Strong. Average length is 16–18 inches.

*Form.*—When first open: High centered. Permanence: Retains its form to the end. Outer petals curl back.

*Petalage.*—Number of petals under normal conditions: 30.

*Color.*—The upper and reverse sides of the petals are Red Group 42A. The base of each petal has on the upper surface a small ¼"×¼" Yellow-Orange Group 17D half moon while on the lower surface of the same sized marking is Yellow Group 12D. The major color on the upper side is Red Group 42A.

*Variegations.*—Occasional white fleck on some petal edges.

*Discoloration*—At the end of the first day: No change. At the end of the third day: No change. By day six or seven, near petal drop on the plant, there is a color change to Red Group 46D.

*Fragrance.*—Slight.

Petals:

*Texture.*—Thick.

*Shape.*—Round to somewhat deltoid.

*Form.*—Tips slightly recurved.

*Arrangement.*—Imbricated. Petaloids in the center: None.

*Persistence.*—Petals drop off cleanly before drying.

*Lastingness.*—On the plant: Long (about seven days). As a cut flower: Long (eight to nine days).

Reproductive parts:

*Anthers.*—Size: Medium. Quantity: Many. Color: Yellow. Arrangement: Regular around styles.

*Filaments.*—Color: Yellow at the base, then red.

*Pollen.*—Color: Gold.

*Styles.*—Color: Red.

*Stigmas.*—Color: Greenish-white.

Plant:

*Form.*—Bush.

*Growth.*—Vigorous; upright; branching. At maturity, height is 4½ to 5 feet, and width is 3½ feet.

Foliage: Number of leaflets on normal mid-stem leaves: Five.

*Size.*—Large; 6 inches long×4½ inches wide.

*Quantity.*—Abundant.

*Color.*—New foliage: Upper and lower surfaces: Greyed-Red Group 178A. Old foliage: Upper Surface: Green Group 139A. Lower Surface: Green Group 138C.

*Shape.*—Broadly oval.

*Texture.*—Leathery; glossy.

*Edge.*—Serrated.

*Serration.*—Single, small.

*Petiole rachis.*—Color: Yellow-Green Group 147C with some Greyed-Purple Group 183A, especially on the upper surface.

*Petiole underside.*—Smooth with occasional prickles.

*Stipules.*—Long (¾"); serrated, bearded.

*Disease resistant.*—Susceptible to mildew and blackspot. Resistance to rust under normal growing conditions.

Wood:

*New wood.*—Color: Greyed-Red Group 178A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked slightly downward.

*Color when young.*—Greyed-Red Group 178A.

*Color when mature.*—Greyed-Orange Group 168D.

Small prickles:

*Quantity.*—On main stalks: None. On laterals: None.

I claim:

1. A new and distinct variety of rose plant of the hybrid tea class, substantially as herein shown and described, characterized particularly as to novelty by its large, bright red flowers; upright, well-branched growth habit; dark green, glossy foliage; and disease resistance to rose rust, but susceptibility to powdery mildew and blackspot.

* * * * *

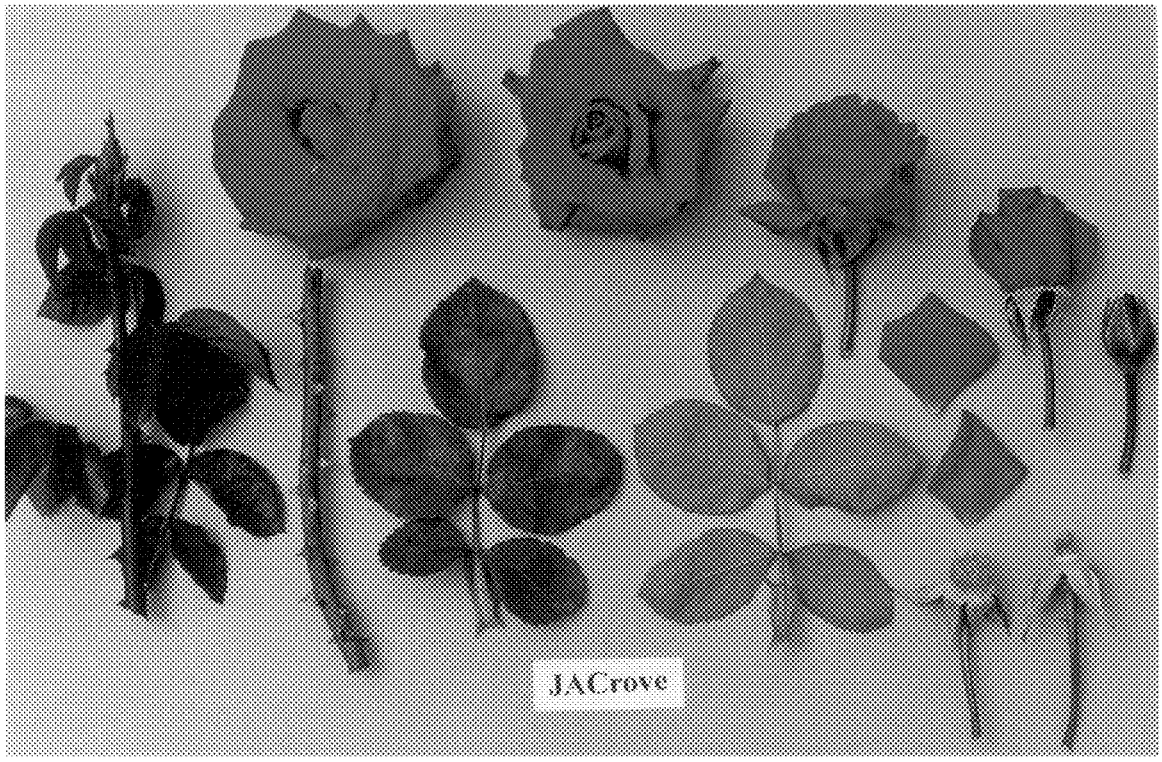
JACrove